(12) United States Patent
Lavallee et al.

(10) Patent No.: US 10,849,694 B2
(45) Date of Patent: Dec. 1, 2020

(54) METHOD AND SYSTEM FOR DISPLAYING THE POSITION AND ORIENTATION OF A LINEAR INSTRUMENT NAVIGATED WITH RESPECT TO A 3D MEDICAL IMAGE

(71) Applicant: IMACTIS, La Tronche (FR)

(72) Inventors: Stephane Lavallee, Martin d'Uriage (FR); Lionel Carrat, Saint Martin d'Heres (FR)

(73) Assignee: IMACTIS, La Tronche (FR)

( * ) Notice: Subject to any disclaimer, the term of this patent is extended or adjusted under 35 U.S.C. 154(b) by 465 days.

(21) Appl. No.: 15/518,885

(22) PCT Filed: Oct. 19, 2015

(86) PCT No.: PCT/EP2015/074183
§ 371 (c)(1),
(2) Date: Apr. 13, 2017

(87) PCT Pub. No.: WO2016/059256
PCT Pub. Date: Apr. 21, 2016

(65) Prior Publication Data
US 2017/0224426 A1 Aug. 10, 2017

(30) Foreign Application Priority Data

Oct. 17, 2014 (FR) .................................. 14306661.1

(51) Int. Cl.
| | | |
|---|---|---|
| *A61B 90/00* | (2016.01) | |
| *A61B 34/20* | (2016.01) | |
| *A61B 17/34* | (2006.01) | |
| *A61B 34/37* | (2016.01) | |
| *A61B 34/00* | (2016.01) | |
| *A61B 34/10* | (2016.01) | |

(52) U.S. Cl.
CPC .......... *A61B 34/20* (2016.02); *A61B 17/3403* (2013.01); *A61B 34/37* (2016.02);
(Continued)

(58) Field of Classification Search
CPC ... A61B 34/10; A61B 34/20; A61B 2034/107;
A61B 2017/3405; A61B 2090/364–368
See application file for complete search history.

(56) References Cited

U.S. PATENT DOCUMENTS 6,296,614 B1 * 10/2001 Pruter ................ A61B 17/3403
600/461
7,215,990 B2 * 5/2007 Feussner ................ A61B 90/36
600/424
(Continued)

FOREIGN PATENT DOCUMENTS

| WO | WO 98/40760 A1 | 9/1998 |
|---|---|---|
| WO | WO 2010/096419 A2 | 8/2010 |
| WO | WO 2010/096419 A3 | 8/2010 |

OTHER PUBLICATIONS

International Search Report and Written Opinion in PCT/EP2015/074183 dated Jan. 5, 2016.
(Continued)

*Primary Examiner* — Angela M Hoffa
(74) *Attorney, Agent, or Firm* — Womble Bond Dickinson (US) LLP (57) ABSTRACT

The invention relates to a method for displaying the position and orientation of a linear instrument (1) navigated with respect to a 3D medical image (V), wherein:
said linear instrument (1) is coupled to a guide (2);
the guide (2) is tracked by a navigation system with respect to the 3D image (V);
a plane (4) containing the axis of the linear instrument (1) is virtually attached to the guide (2);
a slice reformatted in the 3D image and containing said plane (4) is displayed.
Another object of the invention is a system for carrying out said method.

13 Claims, 3 Drawing Sheets

(52) U.S. Cl.
CPC ............ *A61B 90/06* (2016.02); *A61B 90/361* (2016.02); *A61B 90/37* (2016.02); *A61B 2034/107* (2016.02); *A61B 2034/2051* (2016.02); *A61B 2034/256* (2016.02); *A61B 2090/065* (2016.02); *A61B 2090/363* (2016.02); *A61B 2090/368* (2016.02); *A61B 2090/378* (2016.02)

(56) References Cited

U.S. PATENT DOCUMENTS

| | | | | |
|---|---|---|---|---|
| 9,492,097 | B2* | 11/2016 | Wilkes | A61B 5/042 |
| 10,376,179 | B2* | 8/2019 | Parthasarathy | A61M 25/0108 |
| 2005/0251030 | A1 | 11/2005 | Azar et al. | |
| 2009/0076476 | A1* | 3/2009 | Barbagli | A61B 5/1076 604/500 |
| 2009/0221908 | A1 | 9/2009 | Glossop | |
| 2010/0081920 | A1 | 4/2010 | Whitmore, III et al. | |
| 2010/0268067 | A1* | 10/2010 | Razzaque | A61B 18/1477 600/424 |
| 2013/0345718 | A1* | 12/2013 | Crawford | A61B 17/025 606/130 |

OTHER PUBLICATIONS

Search Report in European application No. 14306661.1 dated Jan. 30, 2015.

* cited by examiner

METHOD AND SYSTEM FOR DISPLAYING THE POSITION AND ORIENTATION OF A LINEAR INSTRUMENT NAVIGATED WITH RESPECT TO A 3D MEDICAL IMAGE

FIELD OF THE INVENTION

The invention relates to a method and a system for displaying the position and orientation of a linear instrument navigated with respect to a 3D medical image using a navigation system.

BACKGROUND OF THE INVENTION

Navigation technologies have been widely used to display the position and orientation of instruments on 3D medical images which are Computed Tomography (CT) or Magnetic resonance images (MRI), or any other type such Cone Beam Computer Tomography (CBCT), Positron Emission Tomography (PET), or the like.

Conventionally, a registration method is applied between a 3D image and a tracking device, also named localizer, such that the position and orientation of an instrument is known in a coordinate system attached to the image.

We consider in particular the display of a linear instrument such as a probe, a pointer, a drilling guide, a cannula, a drill bit, a needle, or the like.

Conventionally, the position and orientation of a linear instrument is displayed on several 2D images that represent reformatted slices or projections of the 3D medical image.

In most surgical navigation systems the position of the linear instrument is represented by three views: two views are planes containing the axis of the instrument and are approximately perpendicular to each other, and one view is orthogonal to the instrument axis.

Optionally, a fourth view is displayed, showing a 3D representation of the instrument and images using volume rendering or surface rendering techniques, for example using 3D surfaces of segmented anatomical structures.

In efforts to reduce the complexity and quantity of information which is displayed to the user, some systems have proposed to display only two 2D images containing the linear instrument.

Considering the standard references used in medical imaging, one of those images is often pseudo-axial and the other image is often pseudo-sagittal.

When the user moves the linear tool, the two images are recomputed in real-time to display updates of images that contain the axis of the instrument.

However, none of the representations that are currently available for displaying the position and orientation of a linear instrument in a 3D image are really intuitive, which necessitates training and usage before being efficient.

BRIEF DESCRIPTION OF THE INVENTION

The invention aims at reducing the complexity and number of information for a user who intends to visualize the position and orientation of a linear instrument navigated with respect to a 3D medical image in order to facilitate the insertion of the linear instrument towards a target visible on the 3D image.

An object of the invention is a method for displaying the position and orientation of a linear instrument navigated with respect to a 3D medical image, wherein:

said linear instrument is coupled to a guide;
the guide is tracked by a navigation system with respect to the 3D image;
a plane containing the axis of the linear instrument is virtually attached to the guide;
a slice reformatted in the 3D image and containing said plane is displayed.

According to an embodiment, a representation of the linear instrument is displayed on said reformatted slice.

According to a preferred embodiment, said guide has a non-symmetrical shape and said virtually attached plane is associated with the most longitudinal dimension of the guide.

The linear instrument may be able to slide in the guide. Alternatively, the linear instrument is rigidly fixed to the guide.

According to an embodiment, said reformatted slice is the only view of the 3D image that is displayed.

According to an embodiment, said representation of the linear instrument is a line in the center of said reformatted slice.

Another object of the invention is a system for displaying the position and orientation of a linear instrument navigated with respect to a 3D medical image, comprising:

a processor adapted to be coupled to a navigation system to receive navigation data,
a guide intended to be coupled to the linear instrument and tracked by the navigation system, wherein a plane containing the axis of the linear instrument is virtually attached to the guide so as to allow tracking said plane virtually attached to the guide by the navigation system with respect to the 3D image, the processor being configured to compute a slice reformatted in the 3D image and containing said plane, and
a display coupled to the processor and configured to display said reformatted slice.

According to an embodiment, the guide has a non-symmetrical shape and the virtually attached plane is associated with the most longitudinal dimension of the guide.

The linear instrument may be able to slide in the guide. Alternatively, the linear instrument is rigidly fixed to the guide.

According to an embodiment, the linear instrument is a needle intended to be inserted into a patient's body toward a target, said needle comprising a distal tip and a proximal stop and being able to slide within said guide along a longitudinal axis thereof, and the processor is configured to detect a contact between the needle guide and the proximal stop and to determine, from navigation data of the needle guide when said needle guide is in contact with the proximal stop of the needle and from the length of said needle, a position of the distal needle tip with respect to the 3D medical image;

said system further comprising a user interface coupled to said processor and configured to display, on at least one image of the patient, a representation of the needle and a point on said representation of the needle to represent the needle tip in said determined position.

BRIEF DESCRIPTION OF THE DRAWINGS

Other features and advantages of the invention will be apparent from the following description, in connection with the appended drawings wherein.

DETAILED DESCRIPTION OF EMBODIMENTS OF THE INVENTION

The method described below is carried out by a system comprising a computer and a screen. The computer includes a processor adapted to be integrated or coupled to a navigation system to receive navigation data. The system further comprises a guide coupled to the linear instrument, wherein a plane containing the axis of the linear instrument is virtually attached to the guide so as to be tracked by the navigation system with respect to the 3D image. The processor is also configured to compute a slice reformatted in the 3D image and containing said plane. The screen is coupled to the processor and is configured to display said reformatted slice.

A 3D image of a patient's body comprising a target to be reached by the linear instrument is provided.

The 3D image can be obtained by Computed Tomography (CT), Magnetic resonance (MR), Cone Beam Computer Tomography (CBCT), Positron Emission Tomography (PET), or the like.

The linear instrument can be a probe, a pointer, a drilling guide, a cannula, a drill bit, a needle, or the like. According to an embodiment, the linear instrument is a needle which is intended to perform a biopsy or to treat a tumor using for example radiofrequency, microwave, or cryogeny technics.

Figure 1:
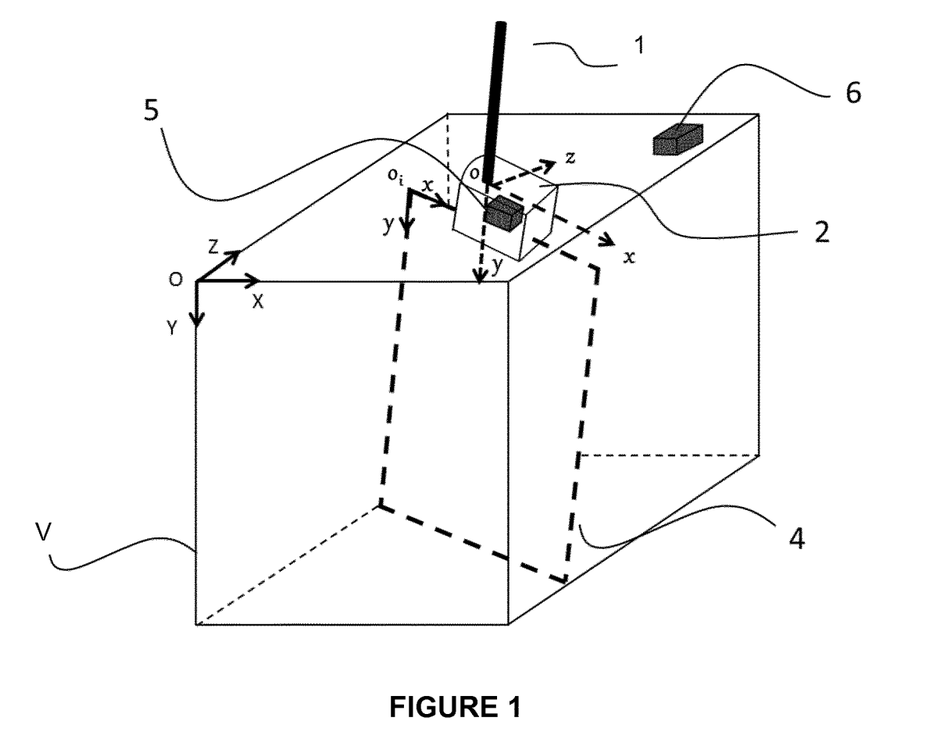
FIG. 1 illustrates an embodiment of the method.

The 3D image is represented by a volume of voxels in a coordinate system represented by (OXYZ) in FIG. 1.

The linear instrument is coupled to a guide.

According to an embodiment, the linear instrument is fixed to the guide. In a particular case, the guide is a very small sensor, such as miniature electromagnetic sensor of less than two millimeters diameter, which can be placed at the tip of the linear instrument.

In a preferred embodiment, the instrument is able to slide and/or rotate inside the guide. The guide can be a needle holder in which a needle can be inserted and slide and/or rotate. The guide can be an adjustable device that has a variable diameter inside, for example using pliers, or it can be made of several cylinders that have different diameters adapted to various needle diameters.

The guide is equipped with a tracker that is localized in position and orientation by a tracking system with respect to the 3D image of the patient. The tracker is localized with respect to a localizer using conventional navigation techniques, said localizer can be for example an electromagnetic emitter placed on the patient and containing fiducials for registering said tracker with said 3D image. Or it can be an optical or electromagnetic localizer or a robot placed on the side of the patient and registered with fiducials placed on the patient or fixed with respect to the examination table.

Globally, the guide has a position and orientation which is tracked in real-time with respect to the 3D image.

The guide may be handled by a user.

Alternatively, the guide can be placed at an extremity of a mechanical articulated arm, a haptic system or a robot.

Using conventional surgical navigation and robotics techniques, the position and orientation of the guide is known with respect to the image coordinate system (OXYZ).

Said position is represented by a local coordinate system (oxyz) and a matrix M between both coordinate systems (OXYZ) and (oxyz) is known at any time.

By convention, it is assumed that the local direction y represents the direction of the linear instrument which is inserted in the guide and o is an origin point located on the axis of the linear instrument.

In conventional surgical navigation systems, planar images containing the linear instrument axis are computed and displayed as oblique slices reformatted in the 3D image volume.

One seeks to display reformatted slices in the 3D image that contain the axis of the linear instrument such that the user can see where the instrument goes on the 3D image with respect to the target. But it is not easy to define and compute a direction d orthogonal to the direction of the instrument y in order to constitute an image plane (o, y, d).

For example, a plane containing the point o, the instrument direction y and the direction X transformed by the matrix M is computed and the corresponding reformatted slice, which is a 2D image, is computed in the 3D image. It constitutes a pseudo-axial view. If the direction z and Z are perfectly aligned, it produces a perfect axial image in a plane parallel to X and Y.

In another example, a plane containing the point o, the instrument direction y and the direction Z transformed by the matrix M is computed and the corresponding reformatted slice, which is a 2D image, is computed in the 3D image. It constitutes a pseudo-sagittal view. If the direction x and X are perfectly aligned, it produces a perfect sagittal image in a plane parallel to Y and Z.

It is common to compute and display two images that correspond to the planes (o, y, X) and (o, y, Z). This provides the user with a simulation of the continuation of the linear instrument before its insertion in the body along two images containing the axis of said linear instrument. The user manipulates the guide and visualizes the images until it is found that the linear instrument will reach the target and avoid obstacles such as dangerous organs. With this mode of representation, the user has to interpret images for which the coordinate systems move together with the guide motion, which may be found difficult by some users.

The proposed method solves this drawback by virtually attaching an image plane to the guide, said image plane containing the axis of the instrument. The position of said attached image plane with respect to the 3D medical image is known via the matrix M. And a reformatted slice corresponding to said plane is computed and displayed on a monitor, which can be of any type including conventional display monitor, small display mounted on any instrument, virtual reality glasses, or augmented reality glasses. In a preferred embodiment, a small display having a size between one to five inches is attached to the guide to offer a complete system that facilitates hand-eye coordination.

The instrument is inserted in the guide along the direction y. For any position of the guide in the image coordinate system represented by a matrix M, a plane passing by the point o, the vector x and the vector y is determined. An image reformatted in the 3D image and containing said plane (o, x, y) is displayed. It produces an effect that is known by physicians when they manipulate an ultrasound probe: the guide acts like a virtual ultrasound probe. With such a representation, a user that has been trained previously to manipulate ultrasound probes and images will find that the navigation of the guide in the 3D image is very intuitive, which helps saving time and reinforcing the efficiency of the procedure.

The computation of the oblique slice reformatted in the 3D image volume relies on standard algorithms. It can be done by many methods and has to be optimized such that the computation and the display of the oblique slice are made in real time. This computation is done using the following principles. For each pixel (i, j) of the reformatted image, the coordinate of the corresponding point p in the coordinate system (oxyz) is computed from the pixel size of the image and the position of the point o in the image coordinate system ($o_i$xy) which depends on the width of the image and on the known geometry of the needle guide (the directions of the width and height of the image coincide with x and y vectors. The coordinates of the corresponding point P in the coordinate system (OXYZ) are then computed by using the matrix M. The voxel corresponding to this point can now be computed directly, using the voxel size of the 3D image, and the data to put in the pixel (i, j) of the image can be computed with this voxel data or, if necessary, with some interpolation techniques from the voxels close to the voxel found (for example, linear, trilinear or neighborhood interpolations). This principle described above can be implemented in a processor using many well-known software functions and algorithms. For example, such algorithms can be provided by software libraries such as ITK (Insight Segmentation and Registration Toolkit) and VTK (Visualization ToolKit), developed by Kitware Inc., New York, USA.

In a preferred embodiment, the guide has a non-symmetrical shape. For example, the guide has an elongated shape with two shorter dimensions y and z and one longer dimension x.

In a preferred embodiment, the guide is a needle holder in which the needle can slide freely along the axis y. For example, the guide can be made of pliers that hold the needle with a pressure sufficient to maintain a linear trajectory but small enough to allow a translation of the needle inside the pliers. A representation of the instrument direction y is displayed on the image. The representation can be a plain or dashed line, either fine with a tool tip or infinite. The user can first navigate the guide in an ultrasound-like mode and then once a suitable image plane has been found that contains the target and that offers a safe access path, the needle can be pushed inside the guide in the direction of the target. The user can then acquire new 3D images to check the correction position of the needle with respect to the target. The user can readjust the guide position if necessary and continue the needle penetration in the body by visualizing the image in the plane (o, x, y) attached to the guide.

In a preferred embodiment, the representation of the linear instrument is a line in the center of said reformatted image, which is not possible with an ultrasound probe equipped with a linear guide and offers the advantage to be very intuitive to manipulate. For example, said line is a vertical line that contains the middle point of the image.

This system will act as if the user would manipulate a 2D imaging ultrasound probe with a linear guide physically attached to the ultrasound probe, but with major differences: (a) the image is not an ultrasound image but a high quality CT, CBCT or MR image, (b) there is no ultrasound probe but only a plastic guide equipped with a tracker, (c) the image is not real but virtual, (d) only one 3D image acquisition is necessary to compute as many virtual images as necessary, (d) the needle can be inserted in the middle of the image which is not possible when the ultrasound probe is present.

If the needle has been at least partially inserted into the patient's body, a rotation of the needle guide around the needle allows exploring the tissues surrounding the needle.

If the needle has not yet been inserted into the patient's body, the needle guide can be used as a viewfinder that allows having the needle in the center of the image, which is more comfortable for a user than conventional systems where the needle is on a side of the image.

In a preferred embodiment, said reformatted image is the only view of the 3D image that is presented to the user, which eliminates confusion and offers a system that is very easy to use.

In another preferred embodiment, the linear instrument is rigidly fixed to the guide. For example, the guide can be attached to the top of a needle, or it can be a miniature electromagnetic sensor inserted in a needle. It is then possible to display not only the direction but also the tip of the instrument on the reformatted image. The representation of the instrument contains a point that is calibrated to represent the tip of the instrument.

FIG. 1 illustrates an embodiment of the method.

A volume V of a 3D image that can be for example a CT or CBCT image is provided.

A coordinate system OXYZ is attached to the 3D image V. A localizer 6 is placed in the volume V and is visible in the 3D image. A registration of the coordinate system OXYZ with a coordinate system attached to the localizer 6 allows determining a transformation matrix between the coordinate system of the localizer and the coordinate system of the 3D image.

A guide 2 is represented as a needle holder in which a linear instrument 1 such as a needle can slide along a defined direction y. A local coordinate system (oxyz) is attached to the guide 2. The line (oy) represents the position of the linear instrument. A tracker 5 is attached to the guide 2 and is tracked by a navigation system. Since the localizer 6 is also tracked by the navigation system, the guide 2 is navigated with respect to the 3D image using a combination of transformation matrices.

An image plane 4 containing o, x and y is computed and represented as a reformatted slice in the 3D image V. Said reformatted slice is then displayed on a monitor.

Figure 2:
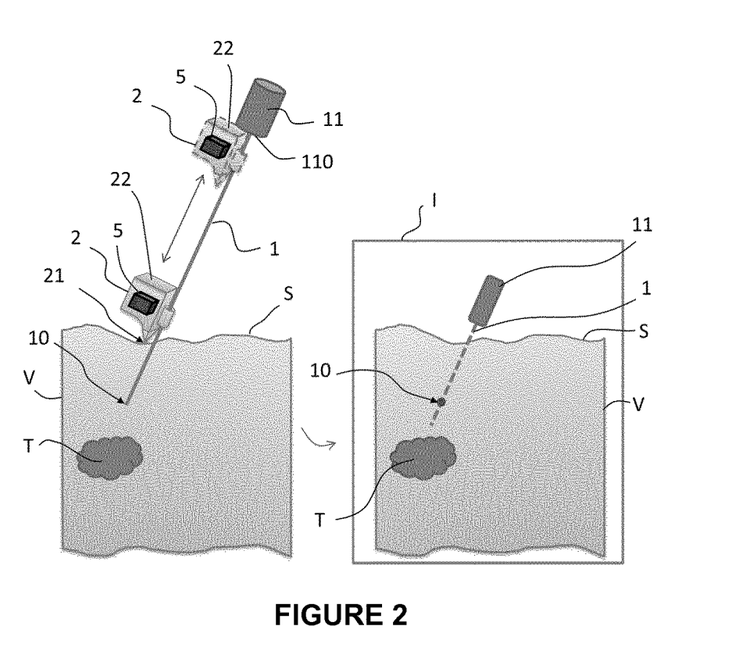
FIG. 2 illustrates the general principle of the determination of the position of the needle tip.

FIG. 2 illustrates how to obtain information on the position of the needle tip.

The left part of the figure shows a volume V of the patient's body delimited by the skin S and comprising a target T to be reached during the surgical intervention.

A 3D medical image of this volume is provided, e.g. by CT, CBCT or by MR imaging.

During the intervention, a user (e.g. an interventional radiologist) uses a needle 1 which is slidingly arranged in the needle guide 2.

The needle guide is equipped with a tracker 5 that is localized in position and orientation by a tracking system. The tracking system can use any appropriate technology of surgical navigation such as electromagnetic, optical, ultrasonic, mechanical, or inertial technologies.

A reference marker (not shown) is attached to the patient's body and is configured to be visible on the 3D medical image. The position and orientation of the reference marker being also known by the tracking system, the needle guide can be navigated with respect to the 3D medical image.

The needle 1 is thus not navigated directly but by means of the needle guide 2. Since the needle can only slide along one direction in the needle guide (and possibly rotate relative to the needle guide), the navigation of the needle guide allows knowing the insertion point (i.e. the point of the tip of the guide 21 when the guide is close to or on the patient's skin through which the needle is inserted) and the direction of insertion of the needle with respect to the 3D medical image.

The guide 2 advantageously presents a tip 21 that is intended to contact the patient's skin or be close to the skin. The maximum accuracy of the navigation is obtained when the guide 2 is as close as possible to the patient, i.e. when the tip 21 is close to or in contact with the skin S. The guide 2 also presents a rear face 22 opposite to the tip 21 in the direction of insertion of the needle. The guide 2 has a known geometry which can obtained during the design and manufacturing process, or by calibration, such that the tip 21 and rear face 22 have known coordinates in the coordinate system of the tracker 5 attached to the guide. The rear face 22 can be very small and assimilated to a point.

The guide may be handled by a user or a tele-operated robot.

The needle 1 comprises a distal tip 10 which is intended to reach the target in view of delivering the intended treatment, and an enlarged proximal portion 11. In particular, the proximal portion 11 comprises a stop 110 that limits the sliding of the needle guide 2 in the proximal direction with respect to the needle 1. By "length of the needle" is meant in the present text the distance between the distal tip 10 and the proximal stop 110. In the present text, the term "proximal" designates a part of the needle that is farthest from the needle tip, and the term "distal" designates a part of the needle that is closest from the needle tip.

In the left part of FIG. 2, the needle guide 2 is represented in two different positions:
 a first position (in plain lines), wherein the tip 21 of the needle guide 2 is close to the skin S—this position (also called "skin position") is considered to provide an optimal accuracy of navigation;
 a second position (also called "stop position") (in dashed lines), wherein the needle guide 2 contacts the stop 110 of the needle at its rear face 22.

By "close to the skin" is meant in the present text that the distance between the needle guide and the skin is smaller than the distance between the needle guide and the proximal stop of the needle. To provide an optimal accuracy of the navigation, this distance should be as small as possible, i.e. the needle guide is in contact with the skin or is at less than 10 mm from the patient's skin.

The double arrow shows the sliding direction of the needle guide 2 with respect to the needle 1.

When the needle guide 2 is in the first position, the position of the needle tip 10 is not known, since the navigation only allows determining the position of the insertion point of the needle on the skin and the direction of insertion of the needle, which corresponds to the axis of the needle guide.

After having inserted partially the needle in the patient body, the user wants to know the distance of the needle tip to the target. To determine the position of the needle tip, the user slides the needle guide 2 in the proximal direction without moving the needle 1, until contacting the stop 110. The stop 110 which is in contact with the needle guide 2 is thus localized by the tracking system.

Provided that the needle length is known, the needle tip 10 can be determined as the point being at a distance equal to said length from the stop 110.

To that end, in an advantageous embodiment, the system may comprise a user interface that is configured to allow the user to enter the length of the needle.

For example, the system can be coupled to a database containing data for a plurality of commercially available needles. Said data may include in particular, for each needle, the length, the diameter, the reference, the manufacturer, etc.

Figure 5:
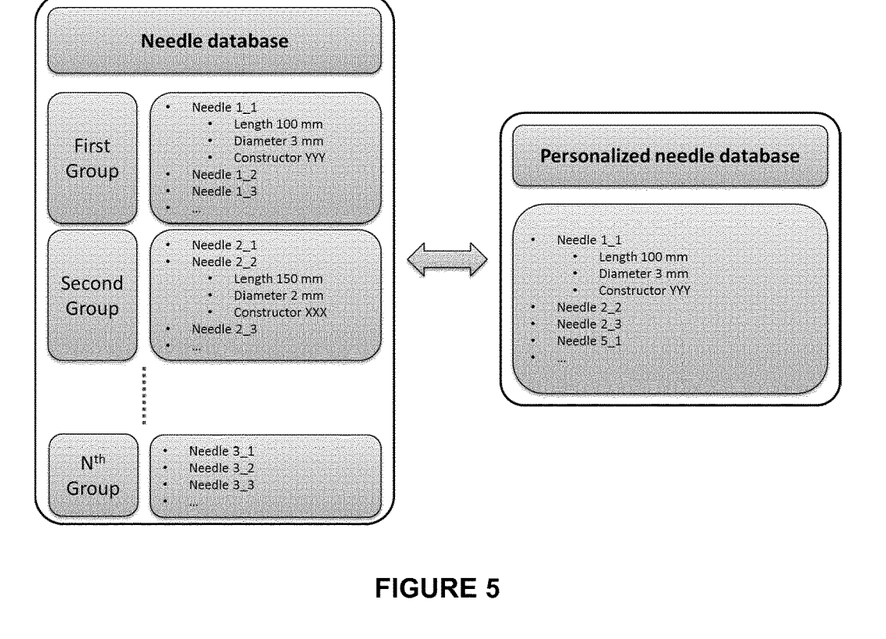
FIG. 5 illustrates schematically a global database for a plurality of needles (left) and a personalized database containing only the data regarding the needles used by the user (right)

FIG. 5 (left part) illustrates an embodiment of such a global database.

Optionally, as shown in the right part of FIG. 5, the system can be coupled to a personalized database containing only the data regarding the needles used by the user. This database can be created by the user as a selection within the above-mentioned global database. Hence, the user interface only displays a limited list of needles that may be selected by the user.

The user interface is also configured to provide information to the user.

This information includes at least one image I of the patient's body which is a slice of the 3D medical image, onto which a representation of the needle 1 is displayed (in dashed lines in the right part of FIG. 3) along with a point (illustrated as a dark disk) identifying the needle tip 10 whose position has been determined as mentioned above. Otherwise, the image can also be the 3D medical image itself or any representation of structures segmented on the 3D image. The tip of the needle can be represented by many possible icons such as a dark disk, a circle, a cross hair, or a partial cross hair.

The system also allows providing information to the user regarding the following facts:
 (i) the optimal accuracy of navigation is obtained when the needle guide is as close as possible from the patient skin;
 (ii) informing the user that the displayed point corresponds to a true representation of the needle tip only when the needle guide is in contact with the needle top, this representation being otherwise incorrect.

This information can be provided to the user using various media. For example, the medium information can be a user's manual, or the above-mentioned user interface with a message, a flag, a color (e.g. green means correct, red mean incorrect), or any specific icon.

Advantageously, the system allows memorizing the position and orientation of the needle guide during the process of determination of the position of the needle tip. The time at which the position and orientation of the needle guide have to be memorized can be determined by the user by interacting with the user interface. In general, the user needs to press a virtual or real button or footswitch to trigger any event, such as memorizing the position and orientation of the needle guide.

This time can also be determined by the processor, by detecting automatically that the needle guide is sliding along the direction of the needle towards the proximal stop of the needle, by analyzing the motions of the needle guide. Indeed, the user has inserted a part of the needle into the patient's body and holds the needle guide close to the skin. When he wants to see the position of the tip of the needle, he slides the needle guide along the needle axis until he reaches the stop in the proximal portion, which produces a stop of the linear motion of the needle guide. The processor detects automatically that the user wants to see the position of the needle tip by using a buffer of some positions and orientations of the needle guide. The processor recognizes in the set of positions and orientations recorded in said buffer a motion pattern corresponding to a line segment followed by a stationary point, and no significant rotation component for such motion, the line segment representing the sliding of the tip point along the needle axis, and the stationary point representing the step when the needle guide is in contact with the needle stop. If such a pattern is detected by the processor, the position and orientation of the needle guide when the needle guide was close to the skin of the patient (i.e. the first position and orientation to memorize) can be computed from the buffer retrospectively, as the very first points of the segment line corresponds to this position. An algorithm to detect such motion pattern can be the following. At any time t, the position P-t is recorded and the past buffer containing for example twenty second of measurements is analyzed. Then the following steps are applied:

(a) Check if the position P-t is stable within a given threshold. If not, iterate to the next point, otherwise continue.
(b) Analyze the past buffer of P-t. Check if it contains a linear motion of the origin point. A linear motion is defined as a set of points that constitute an average line segment with all points being close to the average line within an arbitrary threshold such as two or five millimeters, and which has a minimum elongation above another arbitrary threshold such as two or three centimeters. If not, iterate to the next point, otherwise continue.
(c) Check that the amplitude of rotation components of the positions along the detected line segment is below an arbitrary threshold such as five or ten degrees. If not, iterate to the next point, otherwise continue.
(d) Compute the first position POS1 that corresponds to the beginning of the line segment and the second position POS2 that corresponds to the end of the line segment, positions being ordered by time.
(e) Use POS1 to display the orientation of the needle axis on images.
(f) Use POS2 to compute the needle length and display the corresponding needle tip on said images.

Finally, a sensor can also be put in the proximal portion of the needle in order to automatically detect the time at which the needle guide is contacting the proximal stop of the needle, and then, to retrieve automatically the time at which the orientation and the position of the needle have to be memorized. Such a sensor can be a contact sensor, a force sensor, or a pressure sensor, for example. The sensor is coupled to the processor to communicate to the processor the data acquired by the sensor.

Referring to FIG. 2 (left part), the system memorizes the orientation of the needle 1 when the tip 21 of the guide 2 is close to the skin S. At this stage, the position of the needle tip 10 with respect to the target T is unknown.

Figure 3:
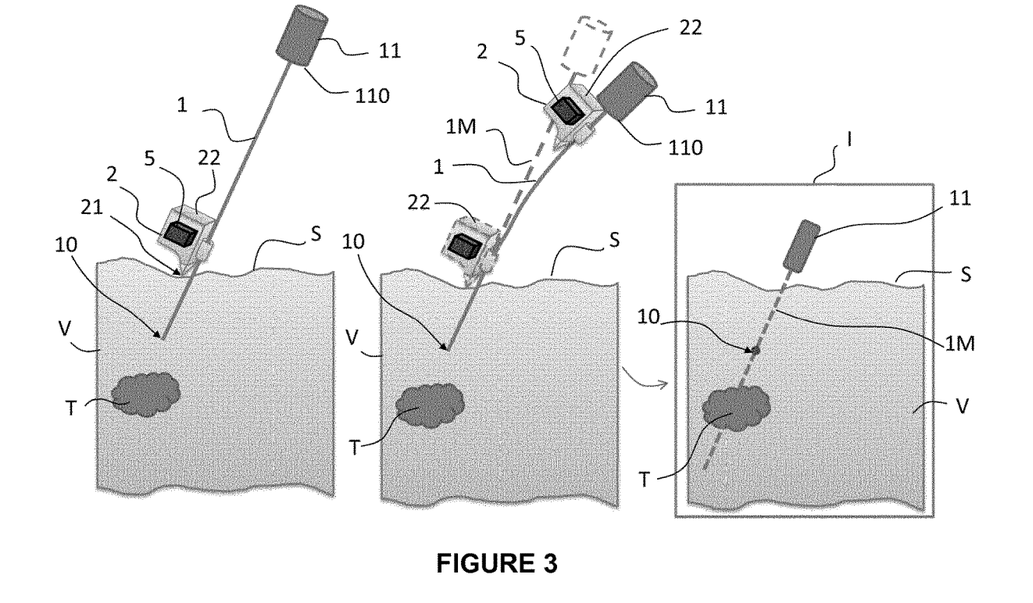
FIG. 3 illustrates successive steps of the invention according to an embodiment wherein the position of the needle is memorized during the process of determination of the position of the needle tip.

Then, as shown in the middle part of FIG. 3, the guide 2 is slid along the needle 1 in the proximal direction. During this operation, the needle 1 may be bent as compared to the memorized orientation 1M shown in dashed lines.

However, as shown in the right part of FIG. 3, a processor computes a projection of the needle 1 on the memorized position and orientation 1M of the needle and uses this projection to compute the position of the needle tip 21 along this memorized orientation of the needle 1M. The point corresponding to the stop 110 of the needle can then be projected on the memorized orientation 1M, and the total length of the needle is used to compute, from the projected point, the position of the needle tip 21.

The processor can also compute a curve connecting the position of the needle when the needle guide 2 is close to the skin S and the position of the needle 1 when the needle guide 2 is in contact with the top of the needle 110. The processor uses the orientation of these positions to compute said curve, using well known spline models for example. Then, the curvilinear distance from the first position to the second position is computed, and is subtracted to the total needle length. The resulting length is used to compute, from the first position, the position of the needle tip on the memorized orientation 1M.

The processor is coupled to the user interface so that the needle tip 10 is displayed in the image I on the memorized orientation 1M of the needle.

Such a projection or computation of the curvilinear distance can be done when the curvature of the needle is limited, i.e. when the distance between the memorized orientation and position of the needle and the orientation and position of the needle when the needle guide contacts the needle stop is less than a given threshold. Said threshold can be a fixed value such as five or ten millimeters for example, or a variable value taking into account the needle length that is not inserted and that is subject to bending.

This distance can be computed by the processor, taking into account the localization data of the needle guide when it is close to the patient's skin and when it is in contact with the needle stop.

Figures 4A, 4B:
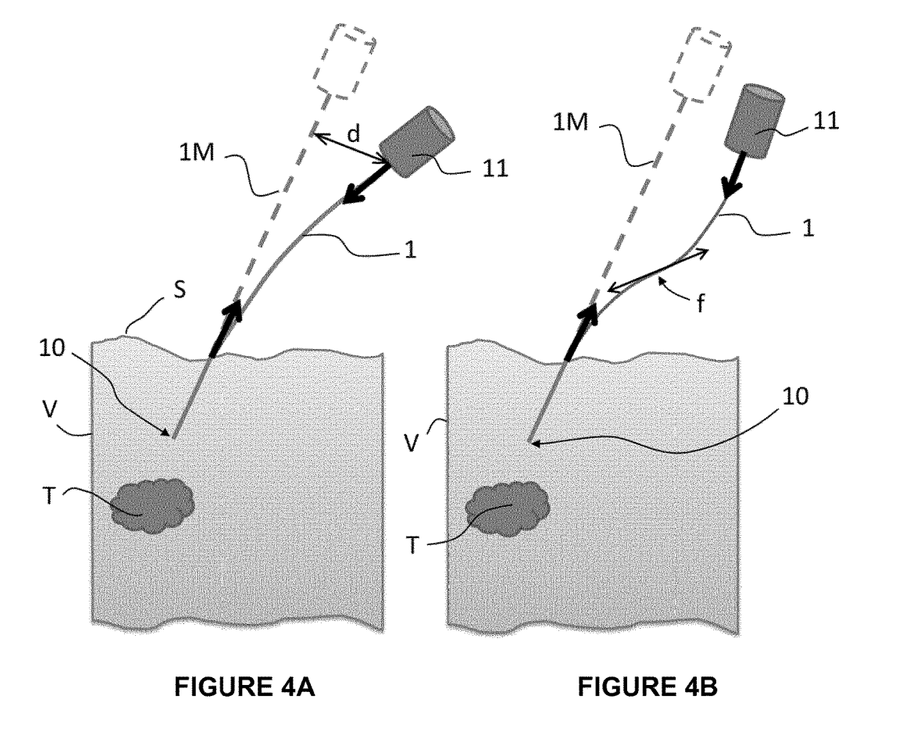
FIGS. 4A and 4B illustrate two situations wherein the user is informed that the position of the needle tip is not displayed accurately.

FIG. 4A illustrates a situation where the distance d between the memorized position and orientation M1 of the needle and the actual orientation of the needle is above said given threshold. In such case, the system informs the user that the displayed point representing the needle tip is not accurate, e.g. by making the displayed needle tip disappear or by sending a flag, a sound or a message to the user.

FIG. 4B illustrates a situation where the needle has an inflection point f. In such case, the projection of the actual needle on the memorized position and orientation is not accurate enough. Hence, the system informs the user that the displayed point representing the needle tip is not accurate, e.g. by making the displayed needle tip disappear or by sending a flag, a sound or a message to the user.

The method described above can be used in many different ways, depending on the user choice and ability. For example, once the needle has been inserted enough in the patient's body, using the method described above, the user may want to visualize constantly the needle tip and not only for a fixed insertion. Therefore, the user can slide the guide until it reaches the stop of the needle and then maintain the guide in this position with respect to the needle, then the user can push the needle and see in real time the tip of the needle progressing on the images. This process can be useful when the needle is approaching to the target in order to stop the needle penetration at a precise location.

In another example, the user can use the method as described above, first placing the guide close to the skin in order to navigate the guide and obtain an optimal accuracy of the targeting direction, inserting the needle partially, second sliding the guide along the needle until the stop has been reached, in order to visualize where is the needle tip, memorize this tip position mentally or using a memory and display of the computer, or simply noting that he has still a number of millimeters to insert the needle, and then the user can come back to sliding the needle guide close to the skin, and push further the needle in the guide in order to benefit from the optimal accuracy of navigation in direction, then he can push the guide again backwards in contact with the needle stop, check the needle tip position, and iterate as many times as necessary.

In order to ensure that the displayed needle tip position is accurate, the needle length is calibrated before carrying out the invention.

Figure 6:
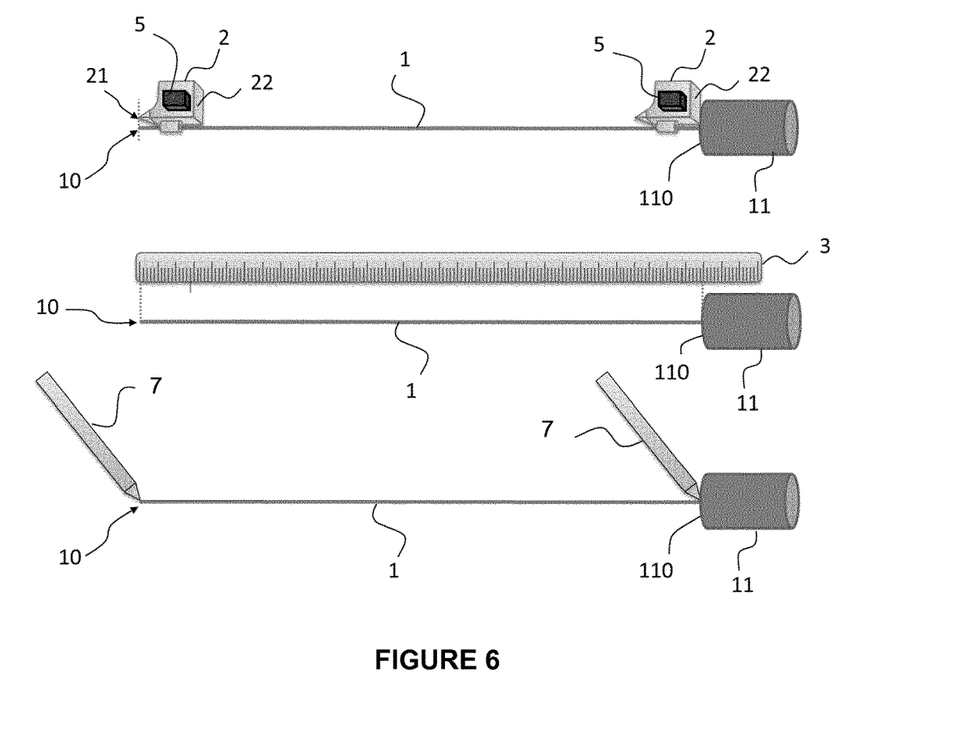
FIG. 6 illustrates different embodiments for calibrating the needle length.

FIG. 6 illustrates different ways of calibrating the needle length, either off-line or on-line.

In the upper part of the figure, the navigated needle guide 2 is used to calibrate the needle length: to that end, the needle guide 2 is positioned successively:
- in a position where the guide tip 21 is at the same level as the needle tip 10 and
- in a position where the rear face 22 of the guide is in contact with the stop 110.

Using the known geometry of the guide, the localization data obtained at said two positions allow determining respectively a first point, which is the tip of the guide in the first position, and a second point which is at the level of rear face of the guide in the second position. The needle is thus equal to the distance between first and second points. During this calibration procedure, the needle has to remain still with respect to the tracking system.

In the middle part of the figure, the needle length is measured by a ruler 3 as the distance between the tip 10 and the stop 110.

In the lower part of the figure, the needle length is determined by pointing successively the tip 10 and the stop 110 with a pointer 7 which is tracked by the tracking system. The localization data obtained at said two positions of the pointer allow determining the length between the tip 10 and the stop 110.

Of course, any other way of calibrating the needle length could be used without departing from the scope of the invention.

Once a needle length has been calibrated, it can be stored in a database together with its other characteristics and a preferred name, given by a user or just reporting the manufacturer name and reference.

The invention claimed is:

1. A method for displaying a position and orientation of a linear instrument navigated with respect to a 3D medical image of a patient's body, the method comprising:
    providing a guide having a non-symmetrical shape, the linear instrument being configured to be coupled to the guide;
    tracking the guide by a navigation system with respect to the 3D image, the guide having a local coordinate system related to a coordinate system of the 3D medical image by a transformation matrix;
    virtually attaching a plane containing an axis of the linear instrument to the guide, a position of the plane with respect to the 3D medical image being determined using the matrix;
    displaying a slice reformatted in the 3D image and containing said plane,
    before coupling the instrument to the guide, forming with the guide a viewfinder allowing visualizing tissues that would surround the instrument if it was coupled to the guide and inserted into the patient's body according to the orientation of the guide, and
    after coupling the instrument to the guide, exploring tissues surrounding the instrument by rotating the guide around the instrument.

2. The method of claim 1, wherein a representation of the linear instrument is displayed on said reformatted slice.

3. The method of claim 1, wherein the plane virtually attached to the guide is associated with a most longitudinal dimension of the guide.

4. The method of claim 1, wherein said linear instrument is able to slide and/or rotate in the guide.

5. The method of claim 1, wherein said linear instrument is rigidly fixed to the guide.

6. The method of claim 1, wherein said reformatted slice is the only view of the 3D image that is displayed.

7. The method of claim 2 wherein said representation of the linear instrument is a line in a center of said reformatted slice.

8. A system for displaying a position and orientation of a linear instrument navigated with respect to a 3D medical image of a patient's body, comprising:
    a processor adapted to be coupled to a navigation system to receive navigation data,
    a guide having a non-symmetrical shape configured to be coupled to the linear instrument and tracked by the navigation system, the guide having a local coordinate system related to a coordinate system of the 3D medical image by a transformation matrix,
    wherein a plane containing an axis of the linear instrument is virtually attached to the guide so as to allow tracking said plane virtually attached to the guide by the navigation system with respect to the 3D image, the processor being configured to determine a position of the plane relative to 3D medical image using the matrix and to compute a slice reformatted in the 3D image and containing said plane, and
    a display coupled to the processor and configured to display said reformatted slice,
    wherein the guide configured so that
    before coupling the instrument to the guide, the guide forms a viewfinder allowing visualizing tissues that would surround the instrument if it was coupled to the guide and inserted into the patient's body according to the orientation of the guide, and
    after coupling the instrument to the guide, a rotation of the guide around the instrument allows exploring tissues surrounding the instrument.

9. The system of claim 8, wherein the plane virtually attached to the guide is associated with a most longitudinal dimension of the guide.

10. The system of claim 8, wherein said linear instrument is able to slide in the guide.

11. The system of claim 8, wherein said linear instrument is rigidly fixed to the guide.

12. The system of claim 8, wherein the linear instrument is a needle configured to be inserted into a patient's body toward a target, said needle comprising a distal tip and a proximal stop and being able to slide within said guide along a longitudinal axis thereof, and wherein the processor is configured to detect a contact between the needle guide and the proximal stop by recognizing a motion pattern of the needle guide corresponding to a line segment followed by a stationary point using navigation data and to determine, from navigation data of the needle guide when said needle guide is in contact with the proximal stop of the needle and from a length of said needle, a position of the distal needle tip with respect to the 3D medical image;
    said system further comprising a user interface coupled to said processor and configured to display, on at least one image of the patient, a representation of the needle and a point on said representation of the needle to represent the needle tip in said determined position.

13. The system of claim 8, wherein the linear instrument is a needle intended to be inserted into a patient's body toward a target, said needle comprising a distal tip and a proximal stop and being able to slide within said guide along a longitudinal axis thereof, the system further comprising a sensor coupled to the processor and configured to detect a contact between the needle guide and the proximal stop, wherein the processor is configured to determine, from navigation data of the needle guide when said needle guide is in contact with the proximal stop of the needle and from the length of said needle, a position of the distal needle tip with respect to the 3D medical image;

the system further comprising a user interface coupled to said processor and configured to display, on at least one image of the patient, a representation of the needle and a point on said representation of the needle to represent the needle tip in said determined position.

* * * * *